United States Patent [19]
Schlager et al.

[11] Patent Number: 6,024,705
[45] Date of Patent: Feb. 15, 2000

[54] AUTOMATED SEISMIC DETECTION OF MYOCARDIAL ISCHEMIA AND RELATED MEASUREMENT OF CARDIAC OUTPUT PARAMETERS

[75] Inventors: Kenneth J. Schlager, Elm Grove; Bruce H. Boehlen, New Berlin; Stephen H. Gorski, Eagle, all of Wis.

[73] Assignee: Bioacoustics, Inc., Milwaukee, Wis.

[21] Appl. No.: 09/188,069

[22] Filed: Nov. 6, 1998

[51] Int. Cl.[7] ................................................... A61B 5/103
[52] U.S. Cl. ............................................................. 600/508
[58] Field of Search ................................... 600/508, 509, 600/510, 511, 512, 513, 514, 515, 528

[56] References Cited

U.S. PATENT DOCUMENTS

| | | |
|---|---|---|
| 4,905,706 | 3/1990 | Duff et al. . |
| 5,109,863 | 5/1992 | Semmlow et al. . |
| 5,159,932 | 11/1992 | Zanetti et al. . |
| 5,255,685 | 10/1993 | Parra . |

OTHER PUBLICATIONS

"Applied Numerical Methods For The Microcomputer" Terry E. Shoup, Prentice–Hall, Inc. Englewood Cliffs, New Jersey 07632, pp. 74–83.

*Primary Examiner*—Scott M. Getzow
*Attorney, Agent, or Firm*—Andrus, Sceales, Starke & Sawall

[57] ABSTRACT

A computer-based instrument to produce a "number" for heart performance parameters and a positive-negative diagnosis of myocardial ischemia. A seismic sensor captures a substantial series of SCG waveforms within a short time frame. Digitized waveforms are created and processed to create signals in the range of 0 to 50 hertz and 0 to 100 hertz. The waveform are processed in the time domain. The 0 to 100 hertz signal is processed to determine the heart rate which is pulse adjusted and interpolated. The SCG waveforms are processed to synchronize the start point of each waveform. The 0 to 50 hertz signal is then processed for signal segmentation to produce waveform signals, each a heart beat or period in length. The segmented signals are then processed to produce linear prediction analysis (LPA) coefficients. The coefficients establish a numerical model-based representation of the waveform. The LPA coefficients in combination contain all of the information resident in the original SCG waveform. For myocardial ischemia analysis, proper LPA coefficients are used in a pattern recognition algorithm to determine a classification of the patent's waveforms as either normal or ischemic. The Bayesian decision classifier provides an analytical framework and program for classification of SCG waveforms as represented by the LPA coefficients for myocardial ischemia, or other cardiac disease conditions represented in the SCG waveform, and produces a direct negative or positive output. For various cardiac performance parameters, estimation rather than a classification algorithm is used such as a K-Nearest Neighbor pattern recognition technology, and multiple regression estimators and produces estimation for different parameters.

38 Claims, 3 Drawing Sheets

AUTOMATED SEISMIC DETECTION OF MYOCARDIAL ISCHEMIA AND RELATED MEASUREMENT OF CARDIAC OUTPUT PARAMETERS

BACKGROUND OF THE INVENTION

This invention relates to seismic detection of myocardial ischemia secondary to coronary artery disease and related measurement of cardiac performance parameters.

Seismic measurement of chest wall vibrations using an accelerometer sensor mounted on the sternum, generates a waveform signal pattern, an example of which is shown in FIG. 2. The seismocardiographic (SCG) waveform, which is the mechanical equivalent of electrocardiographic (ECG) waveform, may be labeled as shown with point features that correspond to the pumping motion of the heart during systole and diastole. The SCG waveform contains information that allows for the noninvasive estimation of various cardiac performance parameters such as ejection fraction (percentage of heart volume pumped on each stroke) and cardiac output (flow in liters per minute). This same SCG waveform also contains information on abnormal heart state conditions such as myocardial ischemia (or angina) in which the heart becomes starved for oxygen because of inadequate blood flow. Myocardial ischemia is a precursor of myocardial infarction (heart attack) in which part of the heart tissue dies because of prolonged oxygen starvation.

SCG technology presents the opportunity to noninvasively measure cardiac performance and detect life-threatening abnormal heart conditions with a single rapid measurement using an operator with minimal medical skills. Current methods of measuring cardiac performance are either extremely invasive (and costly) or noninvasive imaging approaches that require time-consuming measurements and highly skilled operators. Examples of the former invasive techniques are angiographic ventriculography, nuclear ventriculography and right heart catheterization. An example of the latter is echocardiography which provides ultrasonic dynamic images of the heart requiring expert level interpretation. In contrast, with the present invention using SCG, rapid estimation of cardiac performance parameters can be performed rapidly and noninvasively with no requirement for skilled interpretation. A simple readout may provide ejection fraction and cardiac output values in less than one minute of time.

The same situation exists in the detection of myocardial ischemia. Current methods emphasize the use of resting ECG or stress ECG neither of which is very sensitive for myocardial ischemia detection. More sensitive and specific methods such as nuclear (Thallium) imaging are time-consuming, invasive, very costly and require expert interpretation. Again, SCG detection of ischemia can be accomplished quickly, with high sensitivity and specificity and with a simple readout rather than expert interpretation, with the present invention.

Previous attempts at harnessing the power of seismocardiographic waveforms have been handicapped by the lack of advanced instrumentation, signal processing and pattern recognition techniques. Seismocardiography represents the latest development in a general category known as displacement cardiography. This field involves low frequency acoustic measurements in the 0–50 Hz range. The portion of this spectrum below 25 Hz is often called infrasound since it is below the human spectral hearing range. Earlier versions of displacement cardiography were designated as ballistocardiography, kinetocardiography and apexcardiography (Salerno 90). Out of all of these earlier developments, only apexcardiography survives as an auxiliary measurement in occasional use today. The field, however, has an interesting history, and a form of displacement cardiography was employed in monitoring cosmonauts earlier in the Soviet space program. The terms seismocardiography and SCG were coined in 1959 by a Russian physician, B. S. Bozhenko. During the 1960's and 1970's, Dr. Bozhenko and his associates conducted research using crude accelerometers and recording equipment. The technology, however, never received widespread acceptance even in the Soviet Union (Gelis 61). Because of the limited scientific contact between the Soviet Union and West during the Cold War, the Soviet's work on this technology was not known in the West until the late 80's.

SCG technology development in the U.S. has also been limited by the need for expert interpretation. U.S. Pat. No. 4,989,611, which issued Feb. 5, 1991, and U.S. Pat. No. 5,159,932, which issued Nov. 3, 1992, teach the use of SCG technology in cardiac performance evaluation. The '611 patent relates primarily to measurement and display of an averaged SCG waveform. The '611 patent also describes Fourier transform-based processing and a display in the frequency domain. The attending physician must then interpret the results. The '932 patent similarly provides graphic information for detection of myocardial ischemia. Again, the information is presented graphically and must be interpreted by the physician.

Similar experience has been reported in SCG estimation of cardiac performance parameters. Although no known patent literature addresses these functions, informal communications with John Zanetti, a co-inventor of the above two patent disclosures, indicate a preference for using the SCG waveform to estimate various time intervals in the systolic portion of the SCG waveform. These systolic time intervals allow for the use of established formulas to estimate fraction, stroke volume and cardiac output [Harley 69] [Garrard 70]. This approach has two significant shortcomings:

1. It is extremely difficult to automate the identification of marked points on the SCG waveform. Algorithms developed to date have a high error rate due to the wide variation in SCG waveform characteristics.
2. Systolic time interval formulas, while reasonably accurate for most patients, perform very poorly for patients with abnormal waveforms caused by valvular and other heart diseases.

This patent application addresses previous difficulties in automated SCG waveform interpretation for both cardiac performance estimation and myocardial ischemia detection by converting the SCG waveform into the parameters of a mathematical model that accurately represents the SCG waveform and allows for a rapid automated cardiac performance estimation and myocardial ischemia detection in a robust manner without the need of physician or other expert interpretation.

U.S. Pat. Nos. 4,989,611 and 5,159,932, as previously discussed, use SCG technology with the information presented graphically that must be interpreted by the physician.

The SCG waveform, the mechanical equivalent of the well-known electrical ECG waveform, provides information on the functioning of the heart as a pump as opposed to the electrical command signals of the ECG. The SCG waveform records what the heart actually does while the ECG records the signals that direct what the heart is supposed to do.

The present inventor recognized that the waveform structure provided by SCG technology permits formulation of model-based algorithms for cardiac performance measurement and myocardial ischemia detection and therefore avoids the necessity of the visual interpretation of the results by a highly specialized physician and providing, for example, a numerical value for practical clinical application.

Further, although applicable to estimating various diagnostic cardiac performance parameters, SCG has also been recognized as a useful development for detection of myocardial ischemia as noted in the '932 patent.

However, the inventor has recognized the present state of the art includes significant limitations for clinical application. The prior art presentation of visual and therefore subjective information rather than a more definitive objective information has prevented widespread practical application for this technology and particularly non-existent clinical application. Given the continuing emphasis on cost and productivity in the art of cardiac evaluation, the medical community is continuously interested in instrumentation which produce a number relative to a reference to produce a response as to the state of the patient.

SUMMARY OF THE PRESENT INVENTION

The inventor has thus recognized the technology for clinical application requires an improved computer-based automation of an instrument to produce a "number" for heart performance parameters, and particularly a positive-negative diagnosis of myocardial ischemia. In addition, such automation requires an advanced pattern recognition technology, in contrast to prior art pattern recognition based on simple point related-detection such as SCG amplitude ratios and time interval values which does not utilize the full information content of an SCG waveform. The prior system is also critically dependent on accurate SCG point designation. The severity of the latter problem is recognized as particularly formidable in view of the past and current efforts at point identification for simpler ECG waveforms.

The technique described here processes the SCG waveform in the time domain in contrast to techniques which convert the waveform to the frequency domain. Operation in the time domain is necessary to preserve time-related information in the SCG waveform. Transformation to the frequency domain results in the loss of ECG systolic and diastolic time related information.

The present inventor provides instrumentation which includes signal acquisition and processing of an SCG signal without human intervention and converts the SCG waveform into model-based parameters that completely and fully represent the useful information content of the signal, and a pattern recognition processing of such information to detect myocardial ischemia, and produce a useful estimate of the heart performance parameters independent of the need for the prior art necessity for SCG waveform point identification.

The present invention is based on converting the SCG waveform into a set of coefficients that in combination contain the full and complete information resident in the original waveform. The signal sequences identified by the coefficients are then processed in an appropriate pattern recognition processing method and means for classifying of the results of a series of SCG waveforms of a patient. In summary, a series of SCG waveforms are taken of a patient. The series of waveforms are then processed. A signal processor includes a signal processing algorithm which convert each SCG waveform into model parameters and a pattern recognition algorithm that converts the parameters into a substantial and reliable estimate of the cardiac output or other cardiac performance parameters and the diagnosis of myocardial ischemia, by use of proper algorithm.

More particularly, the present invention is disclosed for myocardial ischemia detection as well as for cardiac performance parameter estimation, without reliance of interpretation by the user of a SCG waveform and particularly SCG point designation. In addition, the system further recognizes that the result of any diagnosis and particularly the accuracy of the estimation of cardiac performance is directly related to a recognition of the heterogeneous nature of the patient population.

In a preferred embodiment, the system and method of the present invention includes computer-based instrumentation. Input patient data are recorded. A series of SCG waveforms is generated within a short time frame. Each waveform is similarly processed, and the waveform is digitized and subjected to noise reduction filtering and to low pass filtering to restrict the waveform to the signal in the range of 0 to 50 hertz. The heart rate is then determined followed by SCG screening.

The coefficients are determined, and preferably employing linear prediction analysis, corresponding LPA coefficients to establish a numerical model-based representation of the waveform.

Linear prediction analysis (LPA) provides a program which converts the SCG waveform into a set of filter coefficients that in combination contain all of the information resident in the original SCG waveform.

For myocardial ischemia analysis, the LPA coefficients are used as features in a pattern recognition algorithm to determine a classification of the patent's waveforms as either normal or ischemic. For various cardiac performance parameters, an estimation rather than a classification algorithm is used, and a particularly satisfactory system is K-Nearest Neighbor pattern recognition technology. In the K-Nearest Neighbor system, the parameters of a given unknown sample are estimated based on the values of its adjoining known neighbors. The present inventor recognized that the basic structure of the above system allows the formation of multiple neighborhoods reflecting the diversity of patient populations, each with its own value patterns, and adapts the system as readily and validly used in the estimation of a particular variable, and particularly, the existence of multiple neighborhoods as used in an embodiment of the present invention.

The particulars of one Bayesian Classifier, a Nearest Neighbor parameter estimator as well as regression program estimators are more fully set forth in the illustrated embodiment of the present invention.

The Bayesian decision classifier provides an analytical framework and program for classification of SCG waveforms as represented by the LPA coefficients for myocardial ischemia, or other cardiac disease conditions represented in the SCG waveform.

The K-Nearest Neighbor Estimation program recognizes the heterogeneous nature of the patient population by grouping sample SCG waveforms into clusters for accurate estimation of heart performance parameters and converts the LPA coefficients into estimates of various different heart performance parameters including, but not limited to, ejection fraction and stroke volume.

Although the present teaching is disclosed in an embodiment for myocardial ischemia and other cardiac parameters, the teaching is readily applied to other biomedical applications as well as other nonmedical applications such as, for example, geological applications related to complex waveforms which may result from a physical activity and include information defining the nature of the activity.

In the various applications, the result of the present invention is a more accurate result and a system which can be executed by personnel which are not highly skilled. The system is highly automated and does not require visual interpretation of the output. Further, the system and method is particularly cost effective, particularly for clinical offices and individual practices.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE INVENTION

Figure 1:
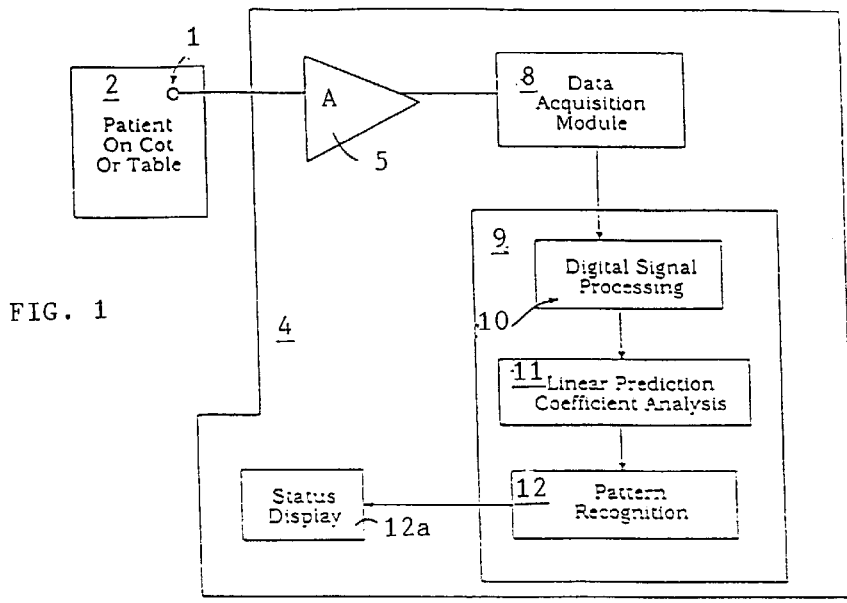
FIG. 1 is a block diagram of a diagnostic system illustrating the basic components of an embodiment of the present invention.
Figure 2:
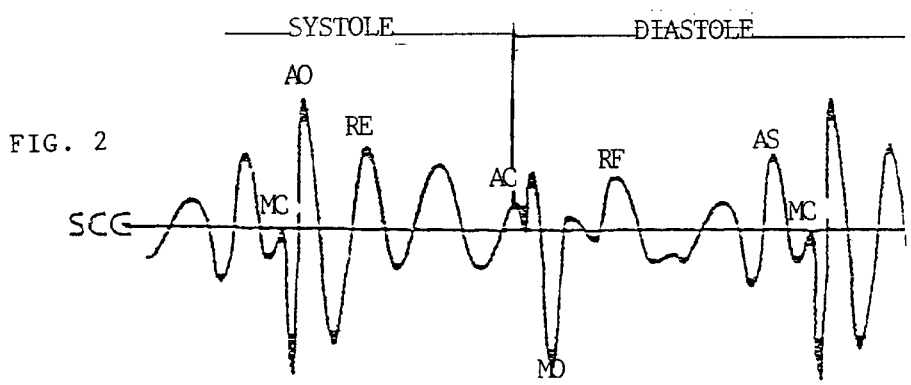
FIG. 2 is a typical SCG waveform of a patient.

An instrument for a seismocardiographic (SCG) analysis of a patient's cardiac performance parameters is shown for clinical application in FIG. 1. Referring to the drawings and particularly to FIG. 1, a sonic (seismic) sensing transducer 1, generally defined as a suitable accelerometer, is secured to the sternum area of a patient's chest 2 just above the xiphoid heart process location. The patient may be placed on a table, cot or other suitable support 3. The sensor 1 is preferably a sensitive and stable accelerometer providing a signal responsive to chest wall vibrations. A typical complex SCG waveform is shown in FIG. 2. The sensor 1 is an input to a computer processing instrument 4. The sensor 1 is connected to a preamplifier 5 which increases the signal level of the accelerometer output. The amplified signals are transmitted to a data acquisition module 8 in which the individual analog signals are converted to digital format for subsequent computer processing.

The time domain sequences of the cardiac seismic signal are converted in the module 8 into digital form and connected to a computer unit 9. In particular, computer unit 9 includes a digital signal processing function 10 programmed to process the digitized waveform and particularly a filtered SCG signal and to create the low frequency acoustic signal in the 0 to 100 Hz and the 0 to 50 Hz range in accordance with known displacement cardiography, remove noise and the like. A special unipolar autocorrelation function is calculated within the processor to determine the heart rate that is required in conjunction with the stroke volume parameter to determine cardiac output. A copy of this special program is attached as a part of an appendix. This information is also necessary to segment the signal sequence received into heart beat time meter values, as more fully described hereinafter.

The processed digital SCG signal is connected within the internal computer program to a linear prediction coefficient determination function 11 in which the LPA coefficients are calculated for time segments of the SCG wave, preferably each segment is a heart beat in length. The average and standard deviation of each of these coefficients are preferably determined, and segments with coefficients beyond a two standard deviation range are discarded. This establishes SCG waveforms as a series of numerical LPA coefficients for processing of the total waveform for classification or for estimation purposes, by selection of the appropriate LPA coefficients.

The SCG waveform coefficients are then processed in a pattern recognition process unit 12 for classification of the SCG waveform and producing an output in one program which identifies a patient with myocardial ischemia. A preferred program is the known Bayesian Classifier which produces a positive or negative status output. The output includes a probability figure indicating the strength of the certainty of the diagnosis to provide more reliable status reports. The status output, and the probability figure when created are outputted to a suitable display 12a, which may be a screen and/or a printed display. Other pattern recognition techniques requiring a smaller patient data base may also be employed for myocardial ischemia detection. Such methods include, but are not limited to, discriminant analysis, K-Nearest Neighbor classification and classification decision trees.

The instrument with the programmed processing of each patient waveform into a series of linear prediction coefficients establishes a basis for accurate comparison with a known class of patient with ischemia and produces a direct status output. The results do not require an operator with a skill above clerical personnel. The instrument is readily produced at an acceptable cost providing a new and highly cost effective instrument. The system and method may also be used for estimation of various cardiac functions by proper selection of LPA coefficients.

Figure 5:
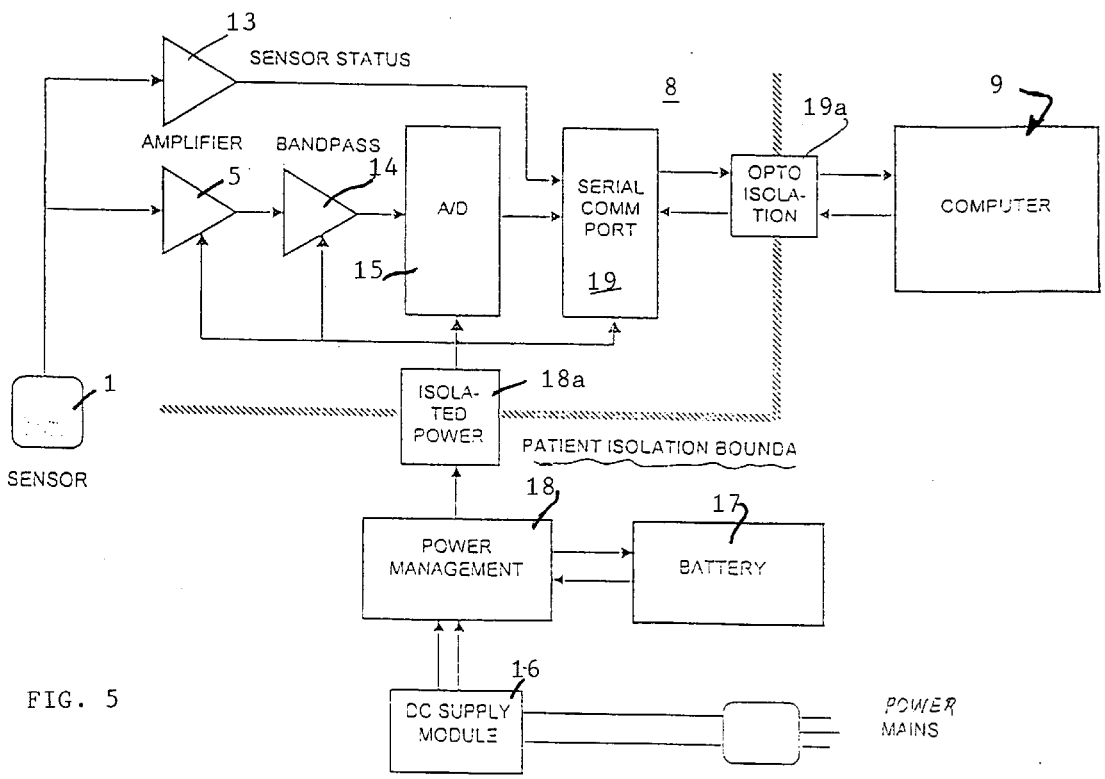
FIG. 5 is a detailed illustration of the signal input section of FIG. 1.

A preferred construction of the module 8 is shown in FIG. 5. A sensor status monitor 13 is connected to sensor 1. A low pass filter 14 may be employed and inserted between the amplifier 5 and an analog-to-digital converter 15. Lowpass filtering may be desirable to remove higher frequency acoustic signals such as heart sounds and murmurs unrelated to SCG analysis. Analog lowpass filters, however, may result in time distortion of the signal and their use has not been found necessary in obtaining highly reliable and satisfactory results with the present invention. Such lowpass filtering is better accomplished after digital conversion of the signal by digital signal processing which provides such filtering without the time distortion of the signal. The other reason for analog filtering as opposed to digital filtering is to prevent a phenomenon known as aliasing in which higher frequency signals appear as a false low frequency signal. Such false signals are not a problem in SCG systems because of the relatively large amplitude of seismic vibrations compared to higher frequency signals.

The output of the amplifier, or lowpass filter where used, is introduced into the Analog-to-Digital converter 15 to digitize the waveform signals.

The A-to-D converter 15 is driven through a suitable DC supply system as illustrated, including a main three phase input to a DC supply module 16 and backup battery supply 17. A power management unit 18 combines the input of the DC supply module and battery supply to insure continuous power availability. A power isolation unit 18a is interposed between the power management unit 18 and the several components of unit 8 to insure total patient isolation from the power supply management system.

The output of the A-to-D converter 15 is connected to a serial communications port 19. The serial communication port 19 is slower than other systems but provides a completely reliable and sufficiently rapid output for diagnostic purposes. An opto-isolation unit 19a is interconnected between the serial communication port 19 and the module 8 and computer unit 9 for processing of the digitized signal. The latter maintains the complete isolation and protection of the patient from the system.

Figure 3:
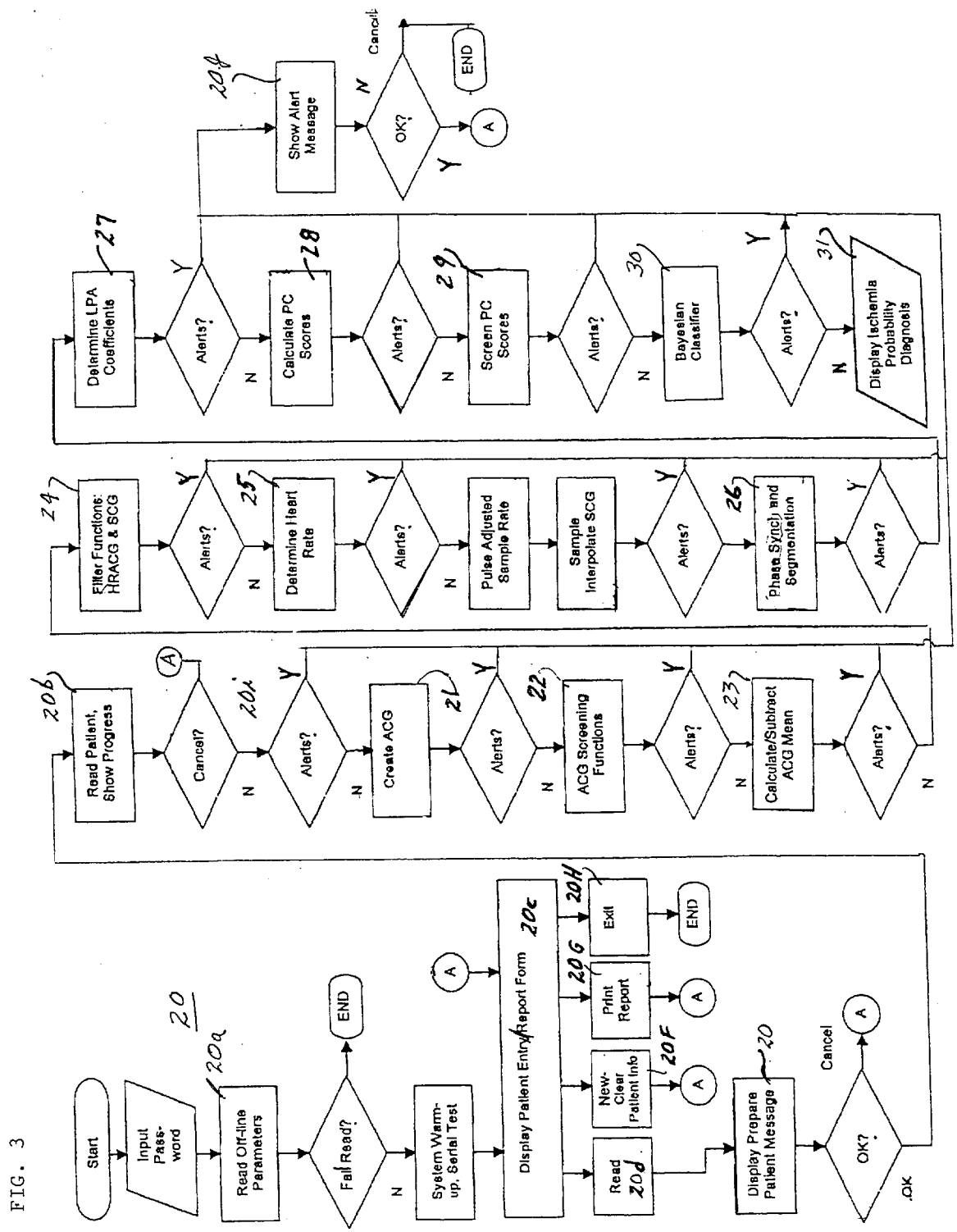
FIG. 3 is a flow chart of a patient's analysis for the detection of myocardial ischemia.

FIG. 3 illustrates a detailed flow chart of a preferred construction with the preferred portion as set forth in the generalized instrument shown in FIGS. 1 and 5 for analyzing the complex SCG waveform shown in FIG. 2, and producing a positive or negative status output for myocardial ischemia.

Figure 4:
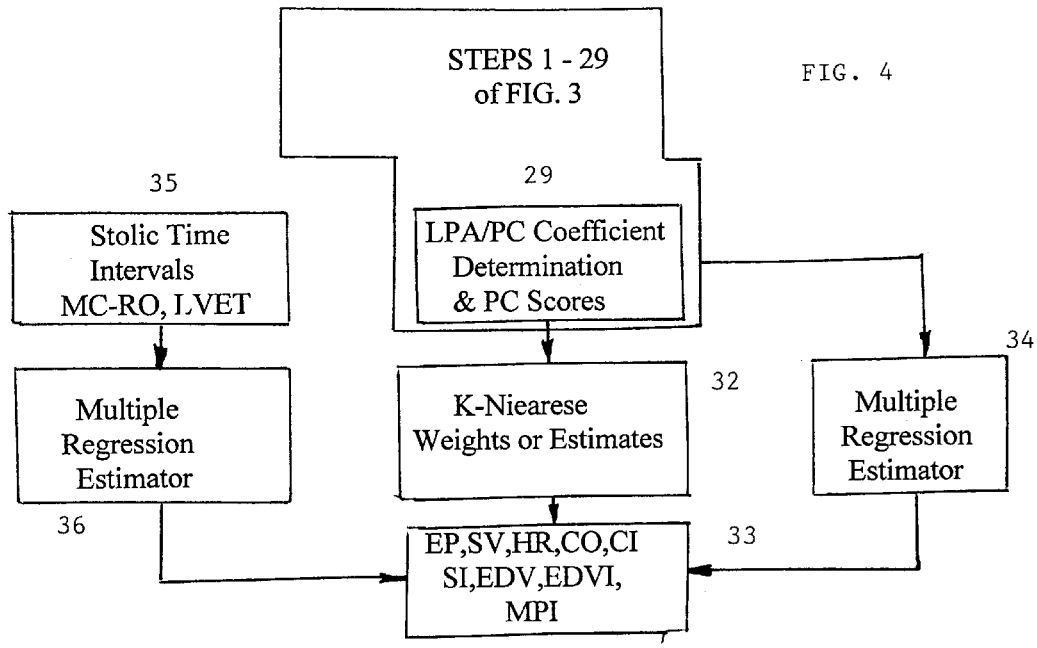
FIG. 4 is a similar flow diagram of the flow chart for an alternate algorithm for multiple cardiac parameter estimation.

FIG. 4 illustrates a similar detailed flowchart for analyzing of the SCG waveform for outputting an estimation of various heart functions.

Referring to FIG. 3, a preferred program includes the inputting and recording of input patient data at step 20.

The Patient Data:

Patient name or code

Sex

Height

Weight

Age

The patient name or code serves as a reference for file designation, storage and retrieval.

Sex of the patient is necessary since some of the algorithm's parameters vary with gender.

Height and weight of the patient are also required to calculate an estimate of body surface area which is used in determining certain cardiac indexes which normalize cardiac output based on body surface area.

Height, weight and age are also used in combination to determine the prior probability of coronary artery disease as an input to the Bayesian Classifier.

In the starting step 20, the noted information necessary to provide an appropriate diagnostic procedure is inputted to the computer along with the model parameters and the patient's waveform as required by the SCG instrument. The program based on this information uses actual samples of the patent's heart action and a set of model parameters provide the necessary information to appropriately classify the patent's heart condition.

The patient data input information is read from an off-line parameter program as at step 20a, the output of which is passed through a processing sequence as shown. Thus, the step 20a output is past through a processing sequence to the "Read" Patient, "Show Progress"20b. The input section 20 also includes a display patent entry/report form program 20c which includes a plurality of programs, which determines and includes a read module which displays a "patients" message as at 20d indicating whether or not it is proper to proceed with the program. The other programs of the module 20c includes a "new" clear patient info 20f, a "print-report" output 20g, an "exit" to end 20h.

The output of the module 20e is first past through a cancel selection, permitting cancellation of the program before stepping to step 20b. If the program is to proceed, an automatic "alert" condition is monitored which detects any condition of the status of the program and if a question arises or is presented, the output is directed to a separate program 20j as shown to present the alert message and allow the operator to appropriately cancel, if necessary, or OK the condition and proceed with the program.

At step 21, the heart SCG signal is inputted and should include a substantial series of the patent's waveforms of the patient; typically may be at a sampling rate of 500 samples/sec. and a period of 10 seconds, producing 5000 waveform samples. The samples are taken and recorded with the patient breathing at a normal quiet level. No separate sensor or reference data for adaptive noise cancellation are necessary.

With the patient accepted, the system operates to sense the output of the chest sensor 1 and creates the series of analog cardiographic (ACG) waveformns. The system monitors such status and determines if any error appears which needs consideration by the operator, as identified by the decision box "ALERT". Such decision points are made throughout the system and are generally hereinafter no longer identified or discussed.

Since the bandwidth of the SCG signal is 0–50 Hz, a sampling rate of 500 Hz is more than sufficient. As previously mentioned, a problem could arise from aliasing signals where signals above 250 Hz appear as false low frequency inputs. However, SCG intensity levels are about two orders of magnitude greater than heart sounds in the over 250 Hz spectral region, so that the aliasing problem should not interfere with the process. An analog lowpass filter could be installed to remove what aliasing effects remain, but such a filter could introduce phase distortion in the SCG signals which would modify the SCG waveform and cause possible significant errors in a Bayesian estimates of cardiac performance parameters as hereinafter discussed.

A noise reduction filter program may processes the SCG waveform. The Adaptive Line Enchancer (ALE) approach to noise reduction may be used. ALE does not require a reference signal for noise reduction. Signal/Noise discrimination is based on the bandwidths of the noise and signal autocorrelation functions. Such a unit is more fully disclosed in the reference of Orfanidis, S. J. *Optimum Signal Processing*, McGraw-Hill 1988, particularly at Pages 429–434 and the Program Number 30 at pages 540–41, 572–73.

The signal-to-noise ratio (SNR) of SCG signals is quite robust at an estimated 20 db level. Further improvement of SNR could, however, enhance both estimation and classification outcomes. For this reason, the ALE filter is an important component of an optimal system. The relative regularity of the SCG cycle also contributes to the efficacy of ALE filtering.

Assuming the analog cardiographic signals are appropriate, the ACG waveforms are digitized and subjected to a screening function as at 22 to pass the low frequency signal, such as previously discussed. After the screening, the digitized ACG signal is centered, as shown by the "calculate/subtract ACG Means" program at step 23. The centered and digitized waveform signal is processed by a filter program 24 to remove the high frequencies and restrict the output signal to a desired frequency band.

At step 24, a low pass filter program removes higher frequency signals not required in SCG analysis. The filter system has a first output in the range of 0 to 100 hertz and a second output in the range of 0 to 50 hertz for the two different signal processes, as hereinafter described.

A FIR digital filter is preferable to a digital IIR filter because of its lack of phase distortion. Phase integrity is very important in a waveform such as the SCG where time intervals contain primary information. The FIR filters, with their uniform phase response, preserves the amplitude-time relationship of the original SCG waveform. Both of these filters results in a vector of weighting coefficients for N previous data points. Different filter coefficients will be used for the analysis of different heart functions, as hereinafter described.

After the filter coefficients are determined in an off-line design program, the on-line FIR filtering program is a simple vector multiplication.

For a FIR filter design program, the McClellan-Parks program in Section 5.1 of IEEE's *Programs for Digital Signal Processing*, (1979) is ideal. This program is in almost universal use in digital signal processing and provides an optimal FIR filter for a given set of specifications using the Remez exchange algorithm. The program may be used for lowpass, highpass or bandpass filters.

For the FIR digital filter program itself, an ideal formulation is contained in Embree's book on *C Language Algorithms for Digital Signal Processing*, Prentice Hall, 1991, pages 145–157. Two programs are included—one for the FIR data array and the other for the actual FIR processing.

At step 25, the program determines the heart rate of the patient from the 0–100 Hz filtered SCG signal and normalizes the heart beat waveform.

A unipolar autocorrelation function can be used to determine heart rate, and has been used successfully in the past. Heart rate is both a primary output in itself and a parameter required for determining cardiac output. Variations in the heart rate are also used in screening for premature ventricular contractions (PVC's) and other arrythmlias, as more fully discussed hereinafter.

The 0 to 100 Hz signal is used to determine the heart rate and the 0 to 50 Hz signal for segmentation and LPA model coefficient determination, as hereinafter described.

For heart rate determination, the autocorrelation function of the SCG waveform is used. The function is basically as follows.

$$R_{xx}(\tau) = \lim_{T \to \infty} 1/T \int_{-T/2}^{+T/2} x(t)x(t+\tau)dt$$

where $R_{xx}$—autocorrelation function $\tau$—lag (shift) time interval $x(t)$—waveform signal The above equation for the periodic SCG waveform are modified to $$R_{xx}(\tau) = 1/T_0 \int_{-T_0/2}^{+T_0/2} x(t)x(t+\tau)dt$$

The integration then is performed over only one time period $T_0$. Converting the above expression to a discrete digital format $$R_{xx}(mT) = 1/N \sum_{k=0}^{N-1} x(kT)x((k+m)T)$$

At time t=kT, the above equation require future samples of x(t). Similar to the analog case, the above equation can be modified so that it only uses past samples of x(t).i.e.

$$R_{xx}(mT) = 1/N \sum_{k=0}^{N-1} x((k-m)T)x(kT)$$

In this equation, T, donates the sampling period and should be chosen to insure that the sampling rate is greater than the signals bandwidth (Nyquist rate). For the sake of simplicity, the factor, T, is usually dropped from the indices of equations $$R_{xx}(m) = 1/N \sum_{k=0}^{N-1} x(k)x(k+m)$$

and $$R_{xx}(m) = 1/N \sum_{k=0}^{N-1} x(k-m)x(k)$$

Where k and m are used to index the samples, the N is the number of correlation points involved. In practice, the correlation size N will depend on the duration of the functions, and on its periodicity if it is periodic.

In the cardiac function analyzer herein, the autocorrelation function composition was modified in the following manner:

1. Positive values only.
   All points on the waveform are expressed as positive (absolute) values.
2. An Envelope function replaces the original waveform. An envelope function (a form of signal smoothing) is formed by connecting a sequence of local maximal points. This avoids effects of any false peaks
3. Envelope autocorrelation The autocorrelation function is then computed from the positive envelope waveform. A 4 second time period in the center of the waveform is used to determine this function.
4. Bias, slope removal and smoothing. Any offset bias or slope is then removed along with a smoothing of the autocorrelation function.

Figure 2A:
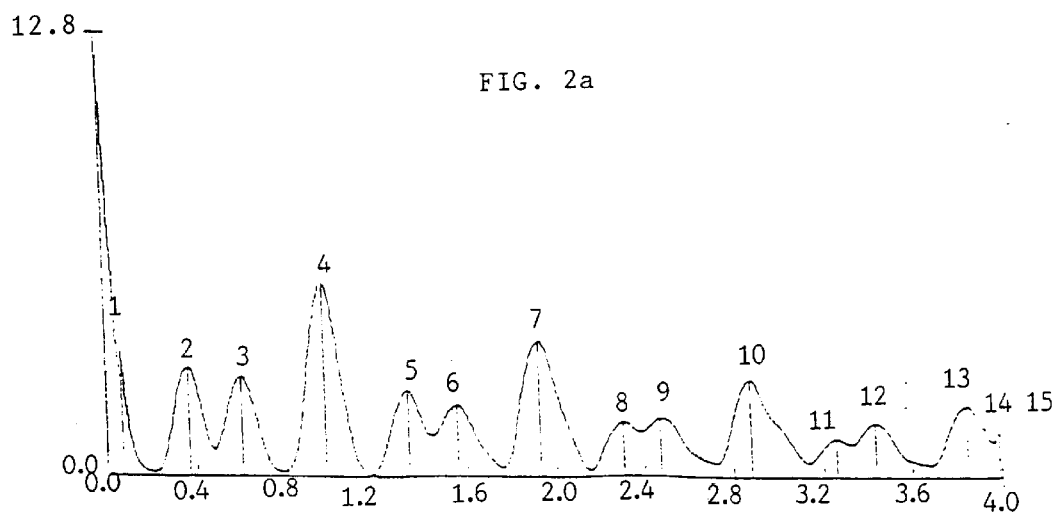
FIG. 2a is a smoothed graphical illustration of a portion of the sample auto-correlation waveforms used to establish the heart rate.

After the above processing is completed, a series of peak points on the modified autocorrelation function are picked and numbered, as shown in FIG. 2*a*. A subset starting with the largest amplitude peak points are then selected to determine the heart period and pulse rate. Observing FIG. 2*a*, points 1, 4, 7 and 10 are selected as the four largest amplitude points. The heart period is then the time period between points 1 and 4 as verified by succeeding periods 4–7 and 7–10 time intervals. The above heart rate algorithm has performed well in comparative testing.

The smoothed graphical output as shown in FIG. 2*a* is in lag time and not real time. The result is a graphical representation of the smoothed heart rate, as shown typically in FIG. 2*a*.

At step 25, the waveform with the heart rate is adjusted and normalized to process a predetermined number of samples per heart beat. For example, in the test runs conducted by the inventor and assignee, an initial system was run at 4500 samples per second and with a ten second monitor or period #5,000 samples were generated. By taking every ninth point, the number of samples in the system for analysis purposes is reduced to 500. To reduce the sampling rate of 500 Hertz to a 100 samples, every fifth point of the last-named sample rate would be analyzed.

In order to provide a proper comparison, a sample interpolation of the patient sample is required in order to analyze the same number of points in the SCG signal for each heart beat. As the heart rate between patients may vary from each other and from the model, it is necessary to interpolate to a common denominator or norm.

Thus, the model SCG waveform is developed with a predetermined number of reference coefficients defining the characteristics of a normal heartbeat. The reference model is referenced to a particular length of a heart beat. In order to develop an appropriate comparison, the patient's waveform must be considered with corresponding coefficients.

The SCG waveform analysis must be based on whole waveform segments one heart beat in length to produce accurate results. Since heart rates vary significantly between patients, compensation for heart rate differences is required. One method of heart rate normalization is based on sample rate variation (Step 25, FIG. 3). If patients with faster heart rates are sampled at a higher rate, then SCG waveform standardization is possible. The following formulas provides normalized SCG waveforms.

SR=500/5 (60/HR)
=100 HR/60
=1.67 HR where

SR—sample rate
—samples/second
HR—heart rate
—beats per minute

Using this variable sampled rate signal, the process then provides for the use of selected number of sampled points for each SCG waveform, typically 100 sampled points, which will provide a single waveform for comparative SCG analysis.

The program then steps to a phase synchronization and segmentation program of the sample waveforms.

The middle four seconds are selected in order to have sliding time divisions and having front and back portions of the waveform for segmenting the ten second signal, as hereinafter described.

At step 26, the wave form information is further processed for the subsequent linear prediction analysis. Linear prediction analysis coefficients, as hereinafter developed, are phase sensitive, so that it is necessary to synchronize the starting point of each SCG wave for analysis purposes. Since SCG point identification is a difficult process, a special windowed cross-correlation coefficient program has been developed to synchronize SCG waveforms, and a copy of this program is attached as a part of an appendix. This program implements a function similar to the classic cross-correlation function except that the correlation values are normalized to calculate a correlation coefficient rather than a sample sliding adjustment necessary to synchronize two SCG waveforms.

$$Max\hat{R}_{yx}(m) = 1/N \sum_{k=0}^{N-1} y(k-m)x(k)/y(k-m)^2 x(k)^2$$

where $R_{yx}m$—cross correlation coefficient
m—lag time=kT
T—sampling period
N—number of correlation points $y'(k)=y(k)-\bar{y}(k)$ $x'(k)=x(k)-\bar{x}(k)$ The role of the primed x and y variables is to remove the bias means prior to crosscorrelation.

The outputs of the program are:
1. Max $\hat{R}_{yx}$
   —the highest correlation coefficient
2. $M_{max}$
   —the lag time of the highest correlation coefficient The $m_{max}$ output is of primary interest for phase synchronization since it represents the time shift necessary to bring the two SCG waveforms into phase alignment.

The cross-correlation program just described will correct the overall phase alignment of two SCG waveforms, but heart beat segments of this waveform may still have phase misalignments because of the varying heart rates of some patients. The phase errors should be small in magnitude as long as waveform segments associated with severe arrhythmias such as premature ventricular contractions (PVCs) are excluded from analysis. Segmental phase error corrections will be further discussed in a later section on LPA coefficient determination. The program designation for phase synchronization is windowed correlation coefficient curve and delay.

After this determination, the 0 to 50 hertz output signal of the lowpass filter is used for signal segmentation and for LPA coefficient determination. At step 26, the ten second original signal sequence is then segmented into a series of waveform signals each of a heart period or beat in length for analysis purposes.

At step 27, the segmented signals are processed to produce linear prediction model coefficients for each heart segment and the mean and standard deviation of each coefficient determined for the sampling period. Coefficients outside of two signal standard deviation ranges are rejected from further processing.

The linear predictions coefficients for the waveform constitutes a signal aspect of the present invention. The process preferably uses the known Burg algorithm.

Each segment of the sampled data stream is converted to a set of LP coefficients that best represent that data stream of that segment. Linear prediction analysis is a well known form of mathematical modeling used to represent a waveform by a relatively small number of model coefficients. The sequential data points of the original waveform are reduced to a substantially smaller number of parameters or coefficients of a mathematical model that will contain substantially all, if not all, of the information resident in the original waveform. These coefficients, which vary for different SCG waveforms, are used to both classify the waveform and/or to estimate other variables related to the heart functioning based on the information contained within the waveform.

Mathematically, the linear predictor is described by the known equation $$X[n]=a_1x[n-2]+ \ldots +a_k x[n-k]=\Sigma a_k x[n-k]$$

where
x [n]—predicted sample at time n
$a_k$—predictor coefficients

It is generally impossible to predict each signal sample exactly and this leads to the prediction error e[n] at each sample time:

$$e[n]=x(n)-x(n)$$

Minimization of the mean squared error between the actual sample values and the linearly-predicted ones allows for a linear solution for determining the value of the predictor coefficients.

The problem in linear prediction is to determine the $a_k$ coefficients so as to minimize the mean square error, E, over a specified number of samples. Now:

$$E = \sum_n e^2[n] = \sum_n [x[n] - x[n]]^2 = \sum_n \left[ x[n] - \sum_{k=1}^{p} a_k x[n-k] \right]^2$$

The number of samples n over which the error is minimized is left unspecified for the moment.

If E is to be minimized by appropriate choice of the $a_k$ coefficients, then the partial derivative of E with respect to each coefficient $a_j, j=1,2, \ldots, p$ should be zero, that is $$\delta E / \delta a_j = -2 \sum_n x[n-j] \cdot \left[ x[n] - \sum_{k=1}^{p} a_k x[n-k] \right] = 0$$

so $$\sum_{k=1}^{p} a_k \sum_n x[n-j] \cdot x[n-k] = \sum_n x[n] \cdot x[n-j], j = 1, 2, \ldots, p$$

The equation provides a basis for establishing a set of P linear equations for P unknown $a_k$.

After the determination of the LPA coefficients for the samples, a program calculates the principal component (PC at step 28) and then screens the principal components at step 29 prior to executing the necessary program for purposes of classifications of the patent's condition. The screening determines if the PC components are outside a normal range to detect a bad run, unusual pattern or other reason to question the validity of the run.

Generally, the equation can be solved by matrix conversion. Three popular and efficient methods of solution include: 1) autocorrelation method; 2) covariance method; and 3) Burg method. Anyone of the methods provides a highly satisfactory result. Applicant has used the Burg method, which those skilled in the art will readily recognize. A reference for all three methods is "Optimal Signal Processing, Orfanidis, S. J." (McGraw Hill, 1988, Section 5.12).

The Burg method has been used because the method is more efficient and accurate for a given time segment of the SCG waveform.

The output solution is based on the form of an L-matrix in which each row of the lower triangular matrix represents an Mth Order LP Model, such as shown in a simplified presentation for M=4.

$$L = \begin{matrix} 1 & 0 & 0 & 0 & 0 \\ a_{11} & 1 & 0 & 0 & 0 \\ a_{22} & a_{21} & 1 & 0 & 0 \\ a_{33} & a_{32} & a_{31} & 1 & 0 \\ a_{44} & a_{43} & a_{42} & a_{41} & 1 \end{matrix}$$

The illustrated L-matrix is of the order of M equal to 4. The accuracy of model prediction depends on the order of the model M. In a practical application for the present cardiac function analyzer, an L-matrix of a much larger size and typically on the order of 50 rows is recommended.

In summary, the program calculates an L-Matrix system from which the target coefficients are selected. The best coefficient combination is determined using the statistical t-values and the multiple correlation coefficient as performance criteria. For classification applications, (ischemia) the row selected is the one with the largest composite t-value, i.e., the row that best discriminates between ischemic and non-ischemic patients. For estimation application (ejection fraction et al., described hereinafter) the row selected is the one with the highest multiple correlation coefficient. The first column of the L-matrix, known as reflective coefficients, is also very effective in some applications.

LPA coefficients are determined and particularly the principal components (PC) are calculated for each time segment, preferably a heart beat in length as previously established. At this step, the average and standard deviation of each coefficient should be determined, and segments with coefficient beyond the 2 standard deviations range should be discarded.

The measure SNR (signal-to-noise ratio) is also determined to provide an overall indicator of measurement performance of the system, as follows:

$SNR = 20\log_{10}(\bar{a}_j / \sigma_j)$

Where
SNR—signal-to-noise ratio
$\bar{a}_j$—average value of coefficient
$\sigma_j$—standard deviation of coefficient The signal processing through step 29 is the same for the classification (shown in FIG. 3) and for estimation (shown in FIG. 4), with proper LPA coefficients selection for each.

Two cardiac observations are screened at step 29 in FIG. 4 using a software program:
 a. Premature Ventricular contractions (PVCT's)
 b. Left Bundle Branch Block (LBBB)

The first screening for PVC's is handled by a standard ECG-based algorithm offered. This algorithm has previously performed well in processing both ECG and SCG, as follows:

1). Calculates the mean heart rate interval for three successive beats (previously preformed).

2). A valid premature ventricular contraction (PVC) is identified if the interval between and two consecutive fiducials in the remainder of the record is less than 80% of previously computed mean heart rate interval.

3). The PVC is identified, and the PVC and the subsequent beat are eliminated

At step 27 of FIG. 3, classification of the waveform based on proper and optimal coefficients, is made to identify the condition of the patient with that of a known class of waveforms related to the presence of ischemia in humans and/or the absence thereof. As noted previously, a Bayesian Classifier provides a particularly satisfactory algorithm in which a sample x is assigned to the class with a highest probability in accordance with the Bayesian decision rule.

Each of the areas of applied mathematics for LPA analysis and the Bayesian Classifier has a signature literature. Only a representative few examples are referenced here.

In linear prediction analysis, the classic source is Markel and Grey {Markel 76}. Although the applications in the book are limited to speech processing, the techniques in theory may be applied to any signal sequence. The problems of speech processing parallel those of biomedical signal processing in their non-stationary nature. SCG signal patterns fluctuate, often significantly, over time. A second important reference is Rabiner and Schafer [Rabiner 78} which covers the same material but in a broader framework of digital signal processing. A number of mathematical techniques are available for converting a time series of signals into linear prediction coefficients. The most popular are the Yule-Walker method and Burg's method {Orfanidis 88}. Burg's method is preferred because of its accuracy for a given order of a LPA filter, and is presented herein.

The literature of Bayesian decision processes is vast, but most of its very theoretical or oriented to business or sociological rather than engineering problems. The best engineering presentation of Bayesian classifiers is found in Tou and Gonzales [Tou 81]. This text provides the backdrop for most of the Bayesian process herein. A true Bayesian classifier requires an extensive database to determine the probability density functions for the particular classification application. With some assumptions regarding the nature of these density functions (such as the normal or Gaussian assumption), a Bayesian implementation is possible with smaller databases. The Bayesian classifier here is all based on original computer programs which are attached as an Appendix to this specification.

Bayesian concepts have been uniquely extended to the above classification problem in a preferred embodiment of the present invention, as follows:

$$p(\omega_i|x) = p(\omega_i)p(x|\omega_i)/p(x)$$

where $p(\omega i|x)$—probability that sample of value x is in class $\omega_i$ $p(\omega_i)$—a priori probability that sample x is in class $\omega_i$ $p(x|\omega_i)$—conditional probability of sample value x if the sample is in class $\omega_I$ $p(x)$—probability that sample will have value x no matter which class it is in.

The basic Bayesian rule, however, is modified by the "Loss" consequences of an erroneous decision. This loss concept fits well with medical diagnosis where a false negative has more serious consequences than a false positive. Losses are expressed in a Loss Function as follows:

$$r_i(x) = \sum_{i=j}^{M} L_{ij} p(\omega_1|x)$$

where $r_i(x)$—Loss when sample x is in class i $L_{ij}$—Loss coefficient when decision selects class j when true class i M—Number of classes The Bayesian classifier integrates the above loss function with the decision rule for a two-class problem as follows:

$$(L_{21})p(x|\omega_2)p(\omega_2) < (L_{12})p(x|\omega_1)p(\omega_1)$$

The sample is assigned to class 2 if the expected loss for an erroneous class 2 decision is less than for an erroneous class 1 decision.
where 2—class=positive sample 1—class=negative sample $L_{21}$—false negative loss coefficient Class 1 is chosen when class 2 is true $L_{12}$—false positive loss coefficient Class 2 is chosen when class 1 is true. Otherwise, it is assigned to class 1. The rule is usually simplified into a form called the Likelihood Ratio:

$$1_{12}(x) = p(x|\omega_1)/p(x|\omega_2) > p(\omega_2) L_{21}/p(\omega_1)L_{12})$$

and $$\theta_{12} = p(\omega_2)L_{21}/p(\omega_1)L_{12}$$

The classification rule then becomes:

1. Assign x to class $\omega_1$ if $1_{12}(x) > \theta_{12}$

2. Assign x to class $\omega_2$ if $1_{12}(x) < \theta_{12}$

3. Make an arbitrary decision if $1_{12}(x) = \theta_{12}$

The Bayesian Classifier is useful only if the parameters of interest can be estimated with a reasonable degree of accuracy. In most instances, it is possible to estimate these parameters quite accurately even with a small size of a database.

The Bayesian Classifier requires the proper estimation of the conditional probability density functions $p(x|\omega_1)$ and $p(x|\omega_2)$.

Two approaches are available for such estimation:

1. Empirical Histogram

Collect sufficient data to provide an imperial density function. In the long run, this approach is the most accurate and will be pursued as the database part of grows in size. The database should be in the hundreds of samples for its effective use.

2. Standard Probability Density Assumption.

Lacking a sufficient data base for an empirical density function, a standard probability distribution such as the normal (gaussian) distribution is used.

Such an assumption allows for the use of the gaussian normal density function:

$$P(x) = (1/\sqrt{2\pi}\sigma)\exp{-[(x-m)^2/2\sigma]}$$

m—mean of function

σ—standard deviation of function.

Since x, σ and m are readily calculated in a current nearest neighbor prototype algorithm, they are easily determined and can be used to calculate the conditional probability of values for any value of x (LPA coefficient) for both positive and negative samples.

Although clinicians may object to the inclusion of prior information in an instrument algorithm and propose relying on the measurement alone, the inclusion is still recommended. In practical terms, it makes no sense to use the same threshold for healthy young applicants as for patients in a cardiac catheterization laboratory. Obviously, the first group has a much lower probability than the second group of having coronary artery disease. The ultimate implementation utilizes the known American Heart Association or Framingharn Study data table to establish prior probability densities based on: age, height/weight and sex.

In the meantime, a current value can also be established based on the population group being tested. If 0.2 (20%) of the patients undergoing examination are at risk for coronary artery disease, then the $p(\omega_I)$ value should be 0.2. If only 0.50 (50%) of a second group are at risk, then $p(\omega_I) = 0.25$. Prior probability density information will improve as the data base and clinical experience grow.

The loss coefficients ($L_{21}, L_{12}$) in combination with the prior density values determine the threshold value ($\theta_{12}$). In the CAD application, the most practical approach is to provide an estimate of the $L_{21}/L_{12}$ ratio. This ratio expresses the relative loss (or human cost) of a false negative to a false positive. For example, if $L_{21}/L_{12}$ is defined as 5.0, then the threshold value $\theta_{12}$ for $p(\omega_2) = 0.25$ would be:

$$\theta_{12} = p(\omega_2)L_{21}/p(\omega_1)L_{12}$$

$$= (0.25)(5)/(0.75)(1)$$

$$= 1.67$$

In other words, the negative conditional probability $p(x|\omega_1)$ must be 1.67 times $p(x|\omega_2)$, the positive conditional probability, before a patient sample is diagnosed as normal (No CAD).

$1_{12}(x) > 1.67$ for a normal diagnosis.

Larger values of $p(\omega_2)$ would increase the $\theta_{12}$ threshold value.

Implementation of a Bayesian Classifier with current data would in summary use the following:

1. Calculate $p(x|\omega_1)$ and $p(x|\omega_2)$ from the empirical histograms.
2. Apply bootstrap statistical testimonies to improve quality of likelihood functions.
3. Designate a prior density value for the patient group of interest.
4. Designate a loss ratio for false negative/false positive.
5. Calculate the likelihood ratio $1_{12}(x)$ and threshold $\theta_{12}$.
6. Assign patient sample based on $1_{12}(x)$ and $\theta_{12}$.

An advantage of the Bayesian Classifier lies in its ability to provide accurate estimates of classification error (accuracy, false negatives and false positives) and the associated system signal-to-noise ratio (SNR) necessary to achieve a given classification error.

The output of Step 30 is a positive or negative status of the patient, with a probability figure indicating the strength of the certainty of the diagnosis. This information is displayed or preferably presented as a written report including the patients name and other pertinent information, at the step 31.

FIG. 4 illustrates an embodiment of the invention for measurement of various heart performance parameters based on various programs including one based directly on a K-NN program in which an estimation of various heart condition and function may be produced.

In the program of FIG. 4, the initial computer program is the same as in the program for ischemia through the generation of the LPA coefficients, as shown at Steps 27–29 in FIG. 3. A modified and proper set of LPA coefficients for particular conditions are used to estimate cardiac parameters.

In one program sequence, a K-NN neighbor program is executed as at 32 to estimate for one or more heart performance parameters, for example, ejection fraction (EV), and stroke volume (SV).

Most patient populations are heterogeneous in nature and an effective set of estimation algorithms should take recognition of this variance. A nearest neighbor pattern recognition (K-NN) provides a first program 32 which by its nature allows for neighborhood clusters. The parameters of a given sample are estimated based on the values of its adjoining neighbors. Such a structure allows for the formation of multiple neighborhoods, each with its own value patterns. The output of the program is outputted as at 33, either as a printed visual display or the like. An excellent summary of the state of the art in nearest neighbor pattern recognition is found in Desrathy as applied to classification rather than estimation [Desrathy 90]. The nearest neighbor (K-NN) pattern recognition technology and program algorithms provide statistical parameters estimation based on the values of its adjoining values.

This allows and establishes evaluation of each sample based on the values of its adjoining samples and particularly allows for analysis of the SCG waveform with formation of multiple neighborhoods, each with its own value pattern. A review of the art relating to K-NN is generally known for classification, as disclosed, for example, in Desrathy's review of subject. Further, Robert's paper on spectrometric estimation in the field of near infrared spectroscopy disclosed an application to spectrometric estimation but does not include multiple neighborhood analysis as used in the present embodiment of the invention.

In the estimation program, the selected LPA coefficients or their principal component counterparts are used as the independent variable inputs to either estimate the cardiac performance parameter (ejection fraction, stroke volume) directly as in K-NN estimation or in other possible programs multiple regression analysis to estimate physiological intermediate variables, such as ejection time that are then in turn used to estimate the cardiac performance parameter.

FIG. 4 illustrates alternative programs for estimation of cardiac performance parameters.

The result is then displayed at the display unit 33 as an estimation number for one or more other references.

Having a highly correlated set of LP coefficients for both EF and SV, there are a number of estimation methods that could be employed in the CFA system from linear regression to artificial neural networks.

A reasonably simple method is a linear multiple regression program, shown at 34 in FIG. 4. Because the modified LP method of feature extraction produces such highly correlated feature variables, it is not necessary to employ more advanced methods which might otherwise be used.

Separate linear multi regression functions have been developed for both EF and SV. The number of modified-LP variables depends on the size of the patient database used to calibrate the regression functions. To date, the maximum number of variables has been the number 5 based on a data base of the number 50–60 patient samples and the number 10 to 1 rule. The number 10 to 1 rule specifies the need for a sample population 10 times the number of variables employed. This rule seeks to avoid overfitting the regression function.

With the selected filter coefficients available, a multiple regression estimator 34 (FIG. 4) is then used to determine and display the values of the two primary parameters (coefficients), for ejection fraction (EF) and stroke volume (SV). Each of these parameters will require its own set of LPA coefficients and its separate regression estimator computation. EF, SV and heart rate are the primary determined variables. The other parameters are derived as follows.

1. Cardiac Output (CO)
   CO=(SV)(HR) L/MIN
2. End Diastolic Volume (EDV)
   EDV=(SV)/(EF) ML
3. Stroke Index (SI)
   SI=(SV)/(BSA) ML/M$^2$
   BSA=0.007184×weight$^{0.425}$(kg)
   ×height$^{0.725}$(cm)
4. Cardiac Index (CI)
   CI=(CO)/(BSA) L/MIN/M$^2$
5. End Diastolic Volume Index (EDVI)
   EDVI=(EDV)/BSA) ML Where:
L=liter
MIN=Minute
ML=Milliliter
M=Meter As shown in FIG. 4, an alternative systolic time interval computation is also possible as a program for cardiac performance parameter estimation. The systolic time intervals, (MC-AO, LVET), are based on modified-LPA coefficients, as at 35. These systolic time intervals along with heart rate are then used to determine the stroke volume, the ejection fraction and the other arrived performance parameter as discussed above, using a regression estimator 36.

Multiple regression analysis is thus used in both of the last two estimation processes shown in FIG. 4.

Various modes of carrying out the invention are contemplated as being within the scope of the following claims particularly pointing out and distinctly claiming the subject matter which is regarded as the matter regarded as the invention.

I claim:

1. A method of rapid, noninvasive automated detection of myocardial ischemia secondary to coronary artery disease in a patient, comprising:

connecting a seismic sensor to the patient and detecting a series of SCG waveforms in accordance with the patient's heart functioning, converting each said SCG waveform into a digital waveform in the time domain, and generating a list of coefficients for said digital waveform containing the complete information resident in said waveform.

2. The method of claim 1 including generating a set of model coefficients of a model SCG digital waveform; comparing said coefficients of said SCG waveform of the patent with said model coefficients to product an output related to said comparison.

3. The method of claim 2 wherein said comparing step includes a computerized pattern recognition program.

4. A method of rapid, noninvasive automated detection of myocardial ischemia in a patient, comprising:

connecting a seismic sensor to the patient and detecting a series of SCG waveforms in accordance with the patient's heart functioning, converting each said SCG waveform into a digital waveform in the time domain, and generating a list of coefficients for said digital waveform containing the complete information resident in said waveform, processing each said filtered digital waveform by segmenting said digital waveform into a substantial plurality of segments, and generating a set of linear prediction coefficients for each segment to define each waveform with the total information resident in the SCG waveform, comparing said defined waveforms using a Bayesian process with model reference SCG waveforms representative of both non-ischemic conditions and ischemic conditions for the presence of an ischemia condition and creating a direct status output for the patient, and presenting said output.

5. The method of claim 4 including the step of processing said linear prediction coefficients with a nearest neighbor program and form multi-neighbor clusters for each said defined waveform.

6. The method of claim 5 including a probability of accuracy.

7. The method of claim 4 wherein said output is a single positive or negative output.

8. The method of measurement of a heart performance parameter of a patient comprising connecting a seismic sensor to the patient and generating a series of SCG waveforms in accordance with the patient heart functioning, converting each said SCG waveform into a digital waveform, filtering said digital waveforms to a frequency of 0–50 Hz., processing each said digital waveform by segmenting said digital waveform into a substantial plurality of segments and generating a set of linear prediction coefficients for each segment to define each waveform with the total information resident in the SCG waveform, and employing a selected subset of these coefficients in a statistical estimation process to estimate cardiac performance parameters.

9. The method of claim 8 wherein said statistics estimation is a K-nearest neighbor process.

10. The method of claim 8 wherein said statistics estimation is a linear regression process.

11. The method of claim 8 wherein said parameter is selected from a plurality of different known heart parameters.

12. The method of claim 8 including the step of processing said linear prediction coefficient with a K nearest neighbor program and form multi-neighbor clusters for each said defined waveforms.

13. The method of detecting a varying and cyclical occurring condition represented by a corresponding continuous complex waveform including a condition complex waveform for each cycle based upon a reference condition complex waveform, comprising generating a selected sequence of condition complex waveforms in said continuous complex waveform, segmenting each said condition complex waveform in said sequence into a substantial number of corresponding segments, developing a set of linear prediction coefficients for each said segment for each said waveform and thereby presenting each said waveform as a series of digital subsignals and presenting a corresponding digitized subsignal containing all of the information of complex waveform, and comparing in a pattern recognition system each said digitized subsignals with reference condition complex waveforms representative of a known condition reference state of said varying and cyclically occurring condition for classifying and varying of said condition with respect to said reference state and cyclically occurring condition.

14. The method of claim 13 wherein a Burg algorithm calculates an L-matrix as a base for selecting said linear prediction coefficient, analyzing said L-matrix for selecting the preferred best linear prediction coefficients in combination for said segments.

15. The method of claim 14 wherein said signal comparing includes the Bayesian parametric system for processing the coefficients of each segment of the digitized signal with said references includes a Bayesian classifier program.

16. The method of claim 15 including a nearest neighbor estimation program to convert said digitized signals for classifying said condition including a possible heterogeneous character of the possible varying conditions.

17. The method of claim 13 wherein said condition waveform is an SCG waveform signal.

18. The method of detecting a varying and cyclically occurring condition represented by a continuous complex waveform of said condition including a plurality of like condition complex waveforms, comprising:

generating a sequence of said condition complex waveforms, segmenting each said continuous condition complex waveform into a substantial number of corresponding and like segments, development a set of linear prediction coefficients for each said segment for each said condition complex waveform whereby each said waveform includes a series of digital subsignals and thereby creating corresponding digitized subsignals containing all of the information of the continuos waveform, establishing a pattern recognition system in which each said digitized subsignal is processed with reference waveforms representative of a known reference condition state of said continuous complex waveform including the varying cyclical occurring condition.

19. The method of claim 18 wherein said developing said set of linear prediction coefficients for each said segment processes a Burg algorithm including calculating an L-matrix as a base for selecting said linear prediction coefficients, and analyzing said L-matrix and thereby selecting the preferred and optimal linear prediction coefficients in combination for each of said segments.

20. The method of claim 19 wherein said comparing and execution of said pattern recognition system includes a Bayesian parametric system for processing and analyzing the coefficients of each segment of the digitized signals with said reference waveforms including execution of a Bayesian classifier program.

21. The method of claim 19 wherein the analyzing of said L-matrix includes a nearest neighbor estimation program for processing said digitized signals to produce a condition signal related to a heterogeneous character of the cyclically occurring condition.

22. The method of claim 18 wherein said condition signal is an SCG waveform signal.

23. The method of claim 18 including providing a seismic sensor to detect the varying and cyclically occurring condition and thereby generating said sequence of said condition complex waveforms, converting each of said SCG waveforms into a digital waveform, filtering said frequency of interest with relation to a condition to be monitored or analyzed, synchronizing the plurality of waveforms to establish a common starting point and each waveform for analysis purposes, determining the original condition rate creating said series of waveforms, normalizing the condition rate to normalize the condition rate represented in said complex waveform and thereafter including said segmenting step and final processing.

24. A method of non-invasive detection of the heart of a patient relative to a known class of patients; comprising:

generating an SCG waveform corresponding to the patient's heart functioning, converting each of said SCG waveforms into a digital waveform, filtering each of said digital waveforms to a first output requency of 0–100 Hz. and to a second output frequency of 0–50 Hz., processing the 0–100 Hz. filtered SCG signal in a unipolar autocorrelation function to determine the repetitive heart rate, synchronizing of the starting point of each SCG waveform for subsequent processing, processing the 0–50 Hz. output frequency signal to segment the signal into a series of segments one heart beat in length and developing the LPA coefficients including the information resident in the original SCG waveforms, and comparing said coefficients with coefficients of the waveform.

25. The method of claim 24 including the step of determining the mean and standard deviation of each linear prediction coefficient and rejecting coefficients outside of at least two signal standard deviation range from further processing.

26. A computer based instrument for the noninvasive detection of the heart condition of a patient relative to a known class of patients, said known class of patient including heart waveforms identified by a set of linear prediction coefficients, comprising:

a signal source configured to sense and generate an SCG waveform corresponding to the patient's heart functioning for a selected period of time, a converter connected to said signal source for converting said SCG waveform into a digital signal, a computer connected to said converter, said computer including:

an input connected to said converter, a filter program for filtering said digital signal to an output signal of a frequency of 0–50 Hz., a program developing LPA coefficients including the information resident in the original SCG waveform of the patient based on said 0–50 Hz. digital signal, and a program comparing said coefficients of said patient's signal waveform with the coefficients of said known class of patients waveform for determining the heart functioning of the patient.

27. The instrument of claim 26 wherein said computer includes a Bayesian classifier program processing of said LPA coefficients of the waveform for ischemic heart status, said Bayesian classifier executing such comparing program and produces a negative or positive or output with respect to the condition of said ischemic condition.

28. The computer based instrument of claim 26 wherein said computer includes a program inclusive of heart waveforms for said known class of patients related to one or more parameters of the heart functioning, said program developing said LPA coefficients developed programs or LPA coefficients related to a selected parameter, and said comparing program determines an estimation of the heart functioning of the patient.

29. The computer based instrument of claim 26 wherein said computer includes a synchronizing program for synchronizing the starting point of the individual heart beat waveform resident in said SCG waveform for processing of said 0–50 Hz. frequency signal.

30. The instrument of claim 29 wherein said computer includes a program for determining the means and standard deviation of each of said linear prediction coefficients and rejecting coefficients outside of at least two standard deviation ranges from final processing and the determination of the execution of the comparing program.

31. The instrument of claim 26 wherein said computer includes a computer program establishing an output frequency of 0–100 Hz., and includes a program executing a heart rate determination program based on said 0–100 Hz. signal, and a program processing said 0–50 Hz. signal to segment the waveform into a series of segments each being one heart beat in length.

32. The instrument of claim 31 including a phase synchronizing program to synchronize the heart signal waveforms within said SCG waveform, said program developing said LPA coefficients being based on said segments of said SCG waveform.

33. The instrument of claim 32 wherein said computer includes a sample rate determination program, said computer executing said sample rate determination program after determination of the heart rate and prior to the execution of said segmenting of the signal into a series of segments.

34. The instrument of claim 32 wherein said computer includes an SCG screening program to screen out premature ventricular contractions and left bundle branch block of the SCG waveform prior to the comparing program.

35. The instrument of claim 26 wherein said LPA related coefficient determination program develops coefficients related to a particular parameter of the heart functioning, said comparing program including a K-Nearest neighbor estimator including coefficients relating to said parameter, and develops and produces an estimation of the actual heart functioning based on the comparison of the known and processed coefficients.

36. The instrument of claim 26 wherein said LPA related coefficient determination program develops coefficients related to a particular parameter of the heart functioning, said comparing program includes a linear regression program for developing the coefficients for a parameter, and said computer including a multiple regression estimation estimator for producing an estimation of the heart parameter functioning.

37. The instrument of claim 26 wherein said LPA related coefficient determination program develops coefficients related to a particular parameter of the heart functioning, said comparing program including a systolic time interval program for detecting or including a resident known coefficients for MC-AO function and the LVET function of a heart, and providing an output related between the known coefficient and the developed coefficients, and a multiple regression estimator providing an estimation output of the actual heart functioning of the patient.

38. The instrument of claim 26 wherein said comparing program generates an output related to the ejection fraction of the heart and the stroke volume of the heart, and includes program for developing of other heart parameters based on said outputs and the heart rate.

* * * * *

UNITED STATES PATENT AND TRADEMARK OFFICE
CERTIFICATE OF CORRECTION

PATENT NO. : 6,024,705
DATED : February 15, 2000
INVENTOR(S) : KENNETH A. SCHLAGER ET AL It is certified that error appears in the above-indentified patent and that said Letters Patent is hereby corrected as shown below:

In The Claims:

CLAIM 2, Col. 19, Line 1, Delete "patent" and substitute therefor --patient--;

CLAIM 2, Col. 19, Line 20, Delete "product" and substitute therefor --produce--; CLAIM 18, Col. 20, Line 56, Delete "development" and substitute therefor --developing--;

CLAIM 18, Col. 20, Line 61, Delete "continuos" and substitute therefor --continuous--;

CLAIM 24, Col. 21, Line 42, Delete "requency" and substitute therefor --frequency--

Signed and Sealed this

Second Day of January, 2001

Attest:

Q. TODD DICKINSON

*Attesting Officer*  *Commissioner of Patents and Trademarks*